United States Patent [19]
Hedgecock

[11] Patent Number: 5,797,854
[45] Date of Patent: Aug. 25, 1998

[54] METHOD AND APPARATUS FOR TESTING AND MEASURING CURRENT PERCEPTION THRESHOLD AND MOTOR NERVE JUNCTION PERFORMANCE

[76] Inventor: James L. Hedgecock, 445 Dartmoor St., Laguna Beach, Calif. 92651

[21] Appl. No.: 509,952

[22] Filed: Aug. 1, 1995

[51] Int. Cl.⁶ .................................................. A61B 5/05
[52] U.S. Cl. .................................... 600/554; 600/391
[58] Field of Search ........................... 128/741, 731–4, 128/422; 604/20

[56] References Cited

U.S. PATENT DOCUMENTS

| | | | |
|---|---|---|---|
| D. 296,470 | 6/1988 | Leopoldi | D24/23 |
| D. 297,168 | 8/1988 | Ioffe et al. | D24/41 |
| D. 299,746 | 2/1989 | Guldalian, Jr. | D24/17 |
| D. 302,302 | 7/1989 | Bell | D24/40 |
| D. 302,303 | 7/1989 | Bell | D24/40 |
| D. 303,430 | 9/1989 | Studer, Jr. et al. | D24/40 |
| D. 319,881 | 9/1991 | Zuppan et al. | D24/214 |
| D. 323,561 | 1/1992 | Bartelt et al. | D24/200 |
| D. 324,106 | 2/1992 | Greenblatt | D24/200 |
| 3,830,226 | 8/1974 | Staub et al. | 128/2.1 R |
| 4,099,519 | 7/1978 | Warren | 128/2.1 R |
| 4,305,402 | 12/1981 | Katims | 128/741 |
| 4,317,457 | 3/1982 | Guillot | 128/783 |
| 4,387,723 | 6/1983 | Atlee, III et al. | 128/734 |
| 4,503,863 | 3/1985 | Katims | 128/741 |
| 4,510,939 | 4/1985 | Brenman et al. | 128/639 |
| 4,515,168 | 5/1985 | Chester et al. | 128/741 |
| 4,541,432 | 9/1985 | Molina-Negro et al. | 128/421 |
| 4,570,640 | 2/1986 | Barsa | 128/741 |
| 4,582,063 | 4/1986 | Mickiewicz et al. | 128/421 |
| 4,586,504 | 5/1986 | de Medinaceli | 128/335.5 |
| 4,590,949 | 5/1986 | Pohndorf | 128/785 |
| 4,595,018 | 6/1986 | Rantala | 128/733 |
| 4,616,660 | 10/1986 | Johns | 128/741 |
| 4,632,117 | 12/1986 | James | 128/421 |
| 4,640,286 | 2/1987 | Thomson | 128/421 |
| 4,693,254 | 9/1987 | Mickiewicz et al. | 128/421 |
| 4,723,152 | 2/1988 | Kenyon et al. | 128/421 |
| 4,759,368 | 7/1988 | Spanton et al. | 128/421 |
| 4,759,377 | 7/1988 | Dykstra | 128/733 |
| 4,763,656 | 8/1988 | Nauman | 128/421 |
| 4,765,343 | 8/1988 | Brenman et al. | 128/639 |
| 4,803,986 | 2/1989 | Dufresne et al. | 128/385 |
| 4,803,988 | 2/1989 | Thomson | 128/421 |

(List continued on next page.)

OTHER PUBLICATIONS

Brochure, "If You're Still Relying . . . ", Int–Med Incorporated, 4pp, 1993.

*Primary Examiner*—Max Hindenburg
*Assistant Examiner*—Pamela Wingood
*Attorney, Agent, or Firm*—D'Alessandro & Ritchie

[57] ABSTRACT

A system is provided for stimulating and measuring performance of nerves which utilizes a novel system of electrodes. A large moistened absorbent pad-type electrode is used to provide one electrical contact with the body. A small moistened absorbent pad-type electrode in a handheld pencil-like configuration is used to provide a second, more targeted electrical contact with the body. By placing the large electrode along or near the spine, the pencil-like electrode may be used to excite and measure nerves on opposite sides of the body. In this manner, the electrical contact made by the large electrode is a constant during the measurement, both as to distance from the tested nerve site, and as to electrical conduction to the body. This arrangement provides more reliable and repeatable measurements. It also avoids patient discomfort associated with needle-like probes, tape-on probes, and other probes which involve discomfort. In another aspect of the invention, a galvanic skin response measurement system is incorporated into the nerve performance measurement system and is used to determine threshold nerve sensing events, rather than relying upon oral input from the patient. In this way, actual events are detected which do not rely for their accuracy upon the truthfulness of the patient. In another aspect of the present invention, the 2000 Hz signal used to stimulate the type A-Beta nerves is amplitude modulated with an adjustable sine wave signal in the range of about 5 Hz to about 700 Hz in order to obtain increased patient sensitivity to the combined signal.

22 Claims, 5 Drawing Sheets

U.S. PATENT DOCUMENTS

| | | | |
|---|---|---|---|
| 4,813,418 | 3/1989 | Harris | 128/421 |
| 4,817,628 | 4/1989 | Zealear et al. | 128/741 |
| 4,848,357 | 7/1989 | Wong et al. | 128/735 |
| 4,892,105 | 1/1990 | Prass | 128/741 |
| 4,926,865 | 5/1990 | Oman | 128/421 |
| 4,932,405 | 6/1990 | Peeters et al. | 128/419 R |
| 4,940,060 | 7/1990 | Gu et al. | 128/735 |
| 4,949,721 | 8/1990 | Toriu et al. | 128/421 |
| 4,957,980 | 9/1990 | Mornings | 604/20 |
| 4,962,766 | 10/1990 | Herzon | 128/741 |
| 4,986,828 | 1/1991 | de Medinaceli | 606/152 |
| 4,989,605 | 2/1991 | Rossen | 128/422 |
| 5,020,542 | 6/1991 | Rossmann et al. | 128/741 |
| 5,046,506 | 9/1991 | Singer | 128/741 |
| 5,092,344 | 3/1992 | Lee | 128/741 |
| 5,131,401 | 7/1992 | Westenskow et al. | 128/741 |
| 5,143,081 | 9/1992 | Young et al. | 128/741 |
| 5,178,145 | 1/1993 | Rea | 128/642 |
| 5,203,330 | 4/1993 | Schaefer et al. | 128/640 |
| 5,255,677 | 10/1993 | Schaefer et al. | 128/640 |
| 5,284,153 | 2/1994 | Raymond et al. | 128/741 |
| 5,291,883 | 3/1994 | Kreutner | 128/421 |
| 5,293,876 | 3/1994 | Koltringer | 128/736 |
| 5,313,956 | 5/1994 | Knutsson et al. | 128/741 |
| 5,327,902 | 7/1994 | Lemmen | 128/734 |
| 5,333,618 | 8/1994 | Lekhtman et al. | 128/734 |
| 5,350,414 | 9/1994 | Kolen | 607/62 |
| 5,363,859 | 11/1994 | Tuckett et al. | 128/739 |
| 5,375,594 | 12/1994 | Cueva | 128/642 |
| 5,388,587 | 2/1995 | Knutsson et al. | 128/741 |
| 5,487,756 | 1/1996 | Kallesoe et al. | 607/118 |
| 5,522,386 | 6/1996 | Lerner | 600/554 |

METHOD AND APPARATUS FOR TESTING AND MEASURING CURRENT PERCEPTION THRESHOLD AND MOTOR NERVE JUNCTION PERFORMANCE

BACKGROUND OF THE INVENTION

1. Field of the Invention

The present invention is directed to a method and apparatus for measuring human nerve integrity through the various sensory nerve fiber groups at any location on the body.

2. The Prior Art

It is often desirable to have a qualitative and quantitative measurement of the ability of a nerve fiber bundle in a human patient to transmit sensory signals. Such measurements are necessary in diagnosing and treating nerve damage. Such bundles may be compromised in a number of ways including: metabolic disfunction (Uremia, Thyrotoxicosis, Hypothyroidism and Diabetes); exposure to toxic substances such as Polychlorinated Biphenyls (PCBs), Dibenzodioxins, Dibenzofurans, Arsenic, Lead, Acrylamide, Organophosphates, and Organic solvents; viral and bacteriological infections such as Human Immunodeficiency Virus, Lyme Disease and Leprosy; hereditary diseases such as Charcot-Marie-Tooth disease and Lawrence-Moon-Bidal Disease; compression and trauma such as Carpal and Tarsal Tunnel Syndrome, Vibration Neuropathy, Radiculopathy and Focal Nerve Lesions; and the like.

Current Perception Threshold (CPT) measurement systems are nerve selective diagnostic stimulators which use essentially painless electrical stimulus applied transcutaneously to evaluate peripheral nerve integrity. Current perception threshold is the minimum current intensity of a nerve specific electrical stimulus that is required in order to produce a sensation. An abnormally high CPT measurement corresponds with a hypoesthetic condition where there is loss or attenuation of nerve function. An abnormally low CPT measurement corresponds to a hyperesthetic condition resulting generally from inflamed, irritated or regenerating nerves. CPT systems have been used effectively in the prior art to provide a measure of nerve disfunction as a result of these types of peripheral neuropathies. The Neurometer® CPT available from Neurotron, Inc. of Baltimore, Md., is an example of such a system. Such systems typically permit a medical professional to test the three basic groups of nerve fiber in the human body. These are type A-Beta, type A-Delta and type C nerves. Type A-Beta nerves are large diameter, rapidly conducting myelinated fibers which the body uses to convey fine sensations such as touch. Type A-Delta nerves are smaller diameter myelinated fibers which are slower conducting and which the body uses to convey coarser sensations such as vibration. Type C nerves are small unmyelinated and relatively slow conducting nerve fibers which the body uses to convey pain and temperature-related sensations. It is well known that type A-Beta nerves are most sensitive to electrical stimulus with a periodicity of about 2000 Hz, type A-Delta nerves are most sensitive to electrical stimulus with a periodicity of about 250 Hz, and type C nerves are most sensitive to electrical stimulus with a periodicity of about 5 Hz.

There is also a great deal of related prior art apparatus for measuring nerve conductance, location and performance. While fit for its intended purpose, much of the prior art suffers from a number of drawbacks which, prior to the present invention, could not be eliminated. For example, much of the prior art relies upon the use of sharp needle-like probes in order to make electrical contact with the human body. See, e.g., U.S. Pat. No. 4,099,519 to Warren. Other prior art makes use of direct physical stimulation, generally requiring a conscious audible response from the patient. This type of direct physical stimulation has been performed in the past with pins, rubber hammers, tuning forks and similar devices. See, e.g., U.S. Pat. No. Des. 296,470 to Leopoldi. An apparatus using mechanical stimulation and recording an electrical signal related to nerve function is described by Dykstra in U.S. Pat. No. 4,759,377. A number of prior art devices make electrical contact to digits of the body (toes, fingers) by use of tape-on or slip-on electrodes. See, e.g., the Neurometer® CPT, U.S. Pat. No. 4,510,939 to Brenman et al. and U.S. Pat. No. 5,203,330 to Schaefer et al. Systems which depend upon patient input in order to determine quantitative or qualitative nerve function are subject to error where the patient either anticipates the test and therefore fails to respond at the correct time, or where the patient, for whatever reason, chooses not to cooperate fully in the test, either by feigning an enhanced nerve response or a decreased nerve response. None of the foregoing prior art references provide a convenient method of measuring bilateral nerve function (i.e., same nerves on opposite sides of the spine) which is patient-friendly, likely to yield comparable results from side to side, and not dependent upon patient audible responses.

SUMMARY OF THE INVENTION

The present invention solves the drawbacks of the prior art.

According to a first aspect of the present invention, a system is provided for stimulating and measuring performance of nerves which utilizes a novel system of electrodes. A large moistened absorbent pad-type electrode is used to provide one electrical contact with the body. A small moistened absorbent pad-type electrode in a handheld pencil-like configuration is used to provide a second, more targeted electrical contact with the body. By placing the large electrode along or near the spine, the pencil-like electrode may be used to excite and measure nerves on opposite sides of the body. In this manner, the electrical contact made by the large electrode is a constant during the measurement, both as to distance from the tested nerve site, and as to electrical conduction to the body. This arrangement provides more reliable and repeatable measurements. It also avoids patient discomfort associated with needle-like probes, tape-on probes, and other probes which involve discomfort.

According to a second aspect of the present invention, a galvanic skin response measurement system is incorporated into the nerve performance measurement system and is used to determine threshold nerve sensing events, rather than relying upon oral input from the patient. In this way, actual events are detected which do not rely for their accuracy upon the truthfulness of the patient or his/her ability to communicate.

According to a third aspect of the present invention, the 2000 Hz signal used to stimulate the type A-Beta nerves is amplitude modulated with an adjustable sine wave signal in the range of about 5 Hz to about 700 Hz in order to obtain increased patient sensitivity to the combined signal.

OBJECTS AND ADVANTAGES OF THE INVENTION

Accordingly, it is an object and advantage of the present invention to provide a nerve performance testing and measurement system with novel electrical probes.

It is a further object and advantage of the present invention to provide a nerve performance testing and measurement system with novel electrical probes which are patient-friendly.

It is a further object and advantage of the present invention to provide a nerve performance testing and measurement system with novel electrical probes which are adapted to provide similar readings from right and left side nerves of a patient.

Yet a further object and advantage of the present invention is to provide a galvanic skin response measurement device in conjunction with nerve performance monitoring in order to provide an electrical signal indicative of a nerve threshold sensing event.

It is a further object and advantage of the present invention to provide a nerve performance testing and measurement system capable of measuring nerve performance in a patient without the results being dependent upon patient truthfulness.

It is a further object and advantage of the present invention to modify the 2000 Hz signal used to stimulate the type A-Beta nerves by amplitude modulating it with an adjustable sine wave signal in the range of about 5 Hz to about 700 Hz in order to obtain increased patient sensitivity to the combined signal.

A key object and advantage of the present invention is that it permits testing to be performed on all spinal dermatome levels and peripheral nerves. It is believed that many, if not all of existing prior art test devices are limited to coverage of Cervical levels C-6, C-7 and C-8, Lumbar levels L-4 and L-5 as well as Sacral level S-1.

Yet another object and advantage of the present invention is to provide more accurate and faster testing than available in the prior art. Some prior art systems use closely spaced electrodes. Since the patient needs to respond when a stimulus is felt, it may be difficult for the patient to discern which electrode delivered the stimulus resulting in an ambiguous result. The present invention eliminates this problem with the large area grounding provided by the ground pad.

These and many other objects and advantages of the present invention will become apparent to those of ordinary skill in the art from a consideration of the drawings and ensuing description of the invention.

DESCRIPTION OF THE PREFERRED EMBODIMENTS

Those of ordinary skill in the art will realize that the following description of the present invention is illustrative only and is not intended to be in any way limiting. Other embodiments of the invention will readily suggest themselves to such skilled persons from an examination of the within disclosure.

The present invention relates to an apparatus for providing both Current Perception Threshold (CPT) testing as well as Somato-Kinetic Motor testing. In conjunction with CPT testing, a galvanic skin resistance (GSR) circuit measures patient skin resistance to detect indicia that a perception threshold has been crossed by the current applied. In this manner, the accuracy of CPT testing is made independent of oral patient responses and is therefore more objective.

Figure 1:
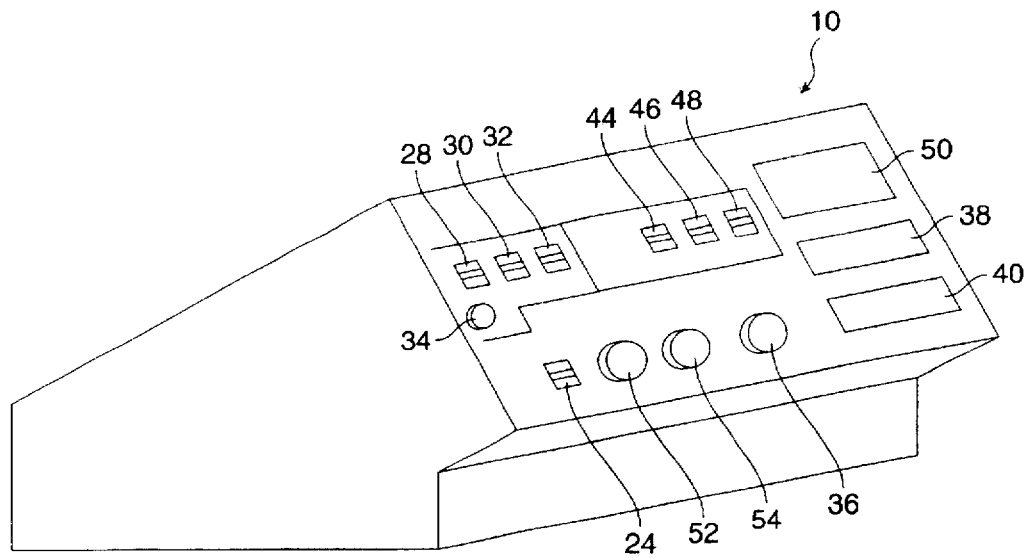
FIG. 1 is a front perspective view of a control unit for a presently preferred embodiment of an apparatus according to the invention.
Figure 2:
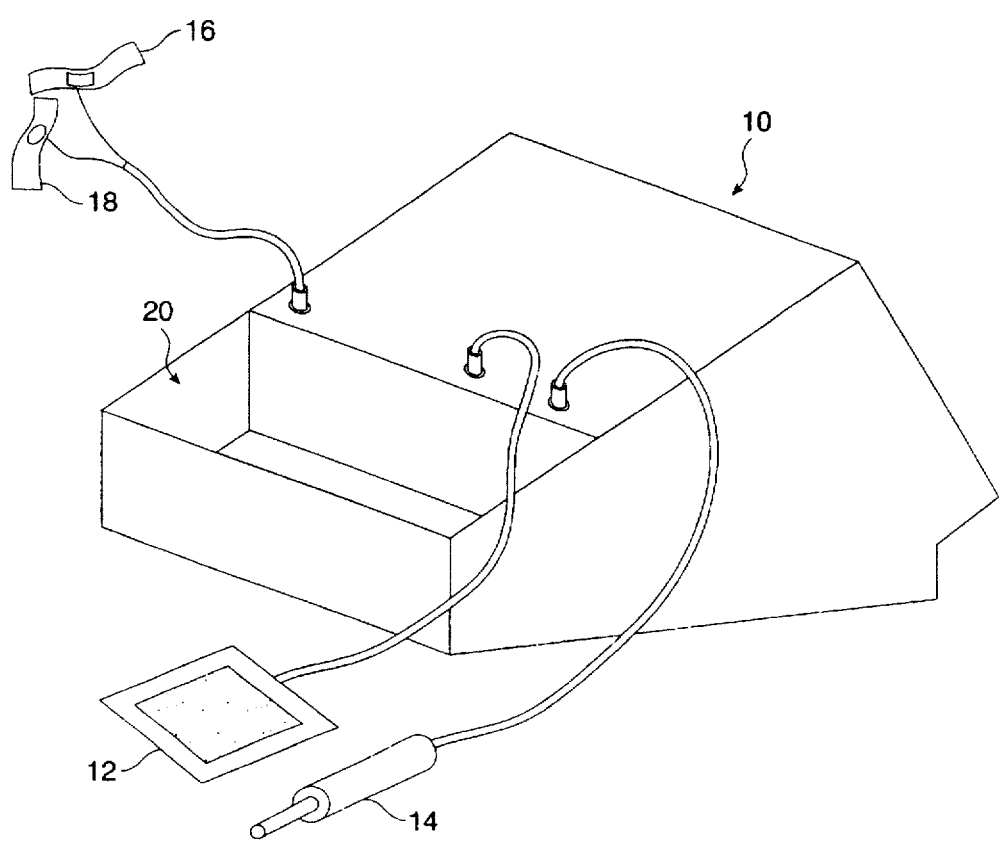
FIG. 2 is a rear perspective view of a control unit for a presently preferred embodiment of an apparatus according to the invention.
Figure 3:
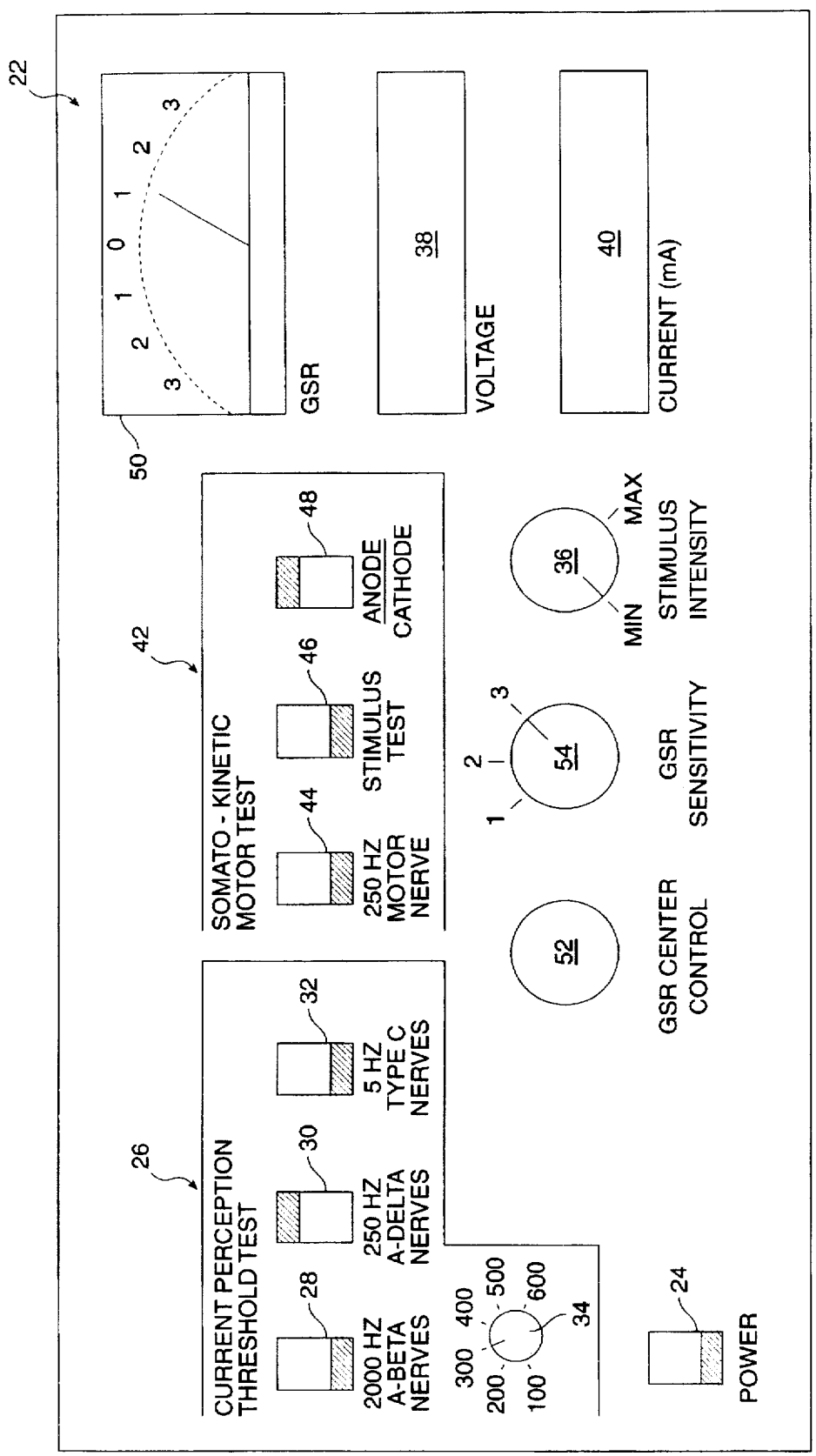
FIG. 3 is a view of the control panel of a control unit for a presently preferred embodiment of an apparatus according to the invention.
Figure 4:
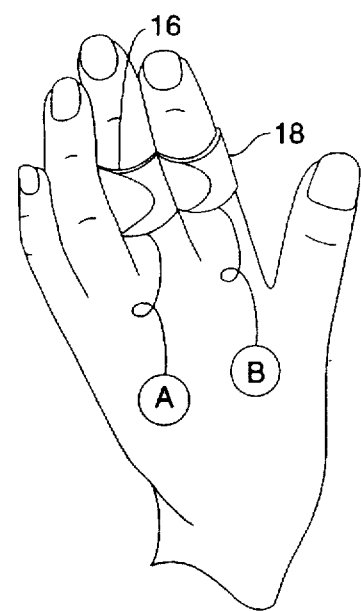
FIG. 4 is a view of a patient's hand coupled to the GSR (galvanic skin resistance) measurement sensors used with a presently preferred embodiment of an apparatus according to the invention.
Figure 5:
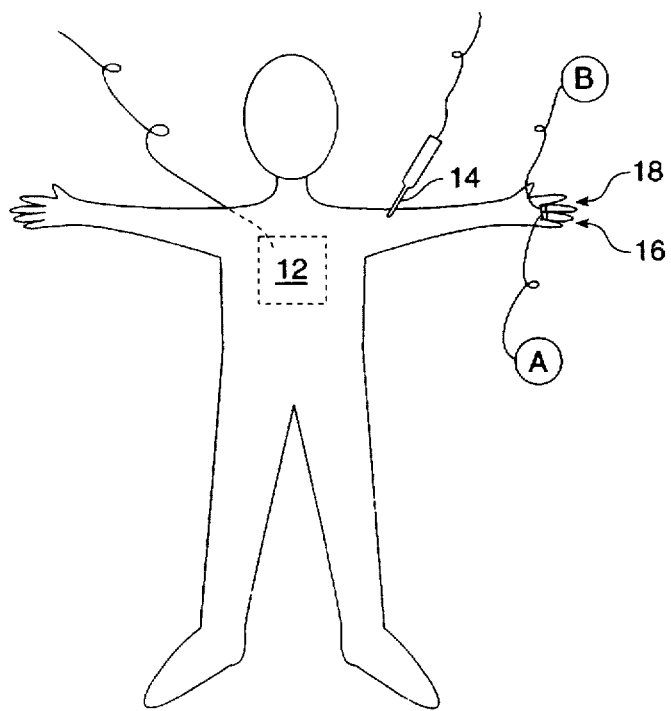
FIG. 5 is a view of a patient showing how the patient would be coupled to the apparatus for testing and measuring current perception threshold and motor nerve junction performance.
Figure 6A:
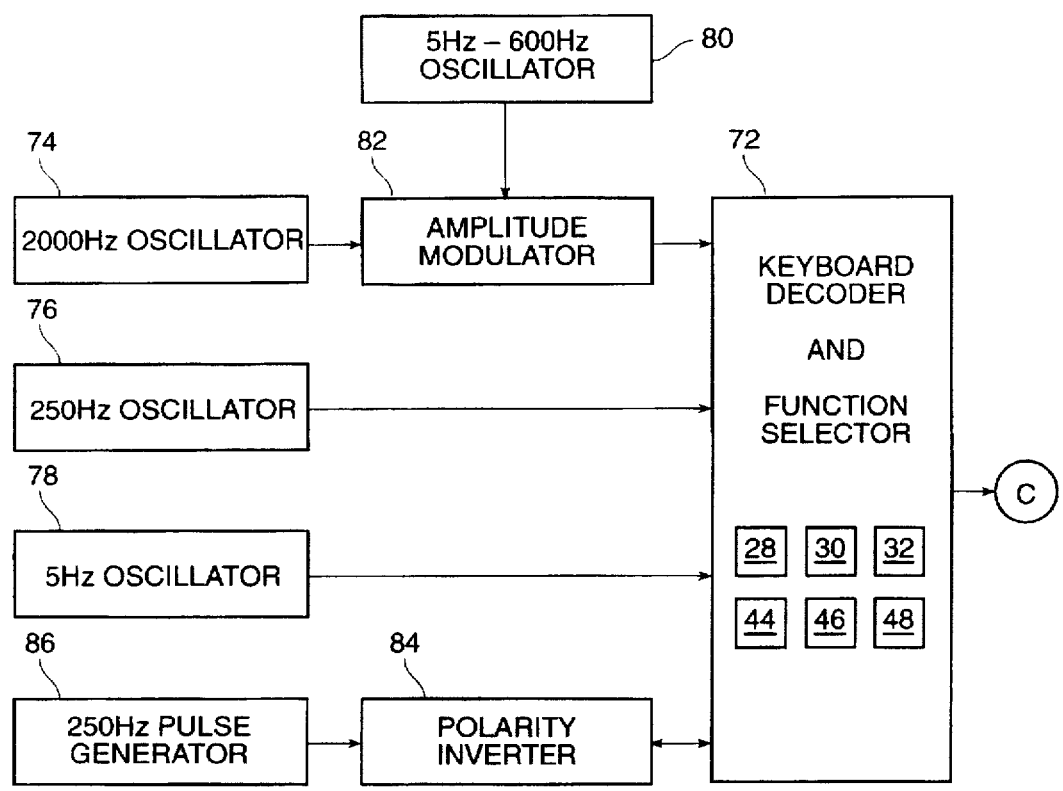
FIG. 6A is a first portion of a schematic block diagram of a presently preferred embodiment of an apparatus according to the invention.
Figure 6A:
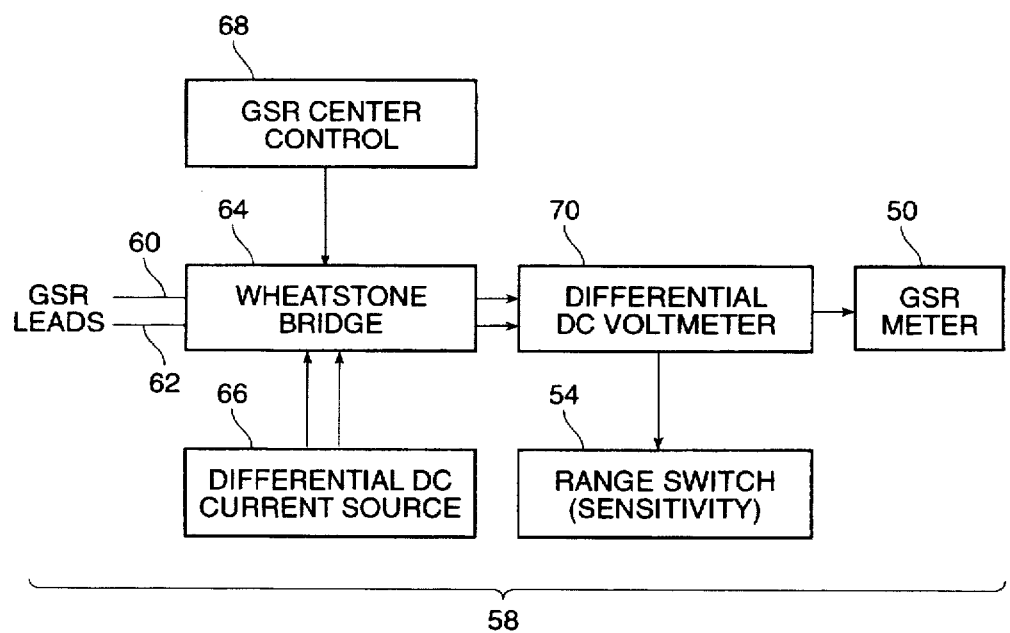
Figure 6B:
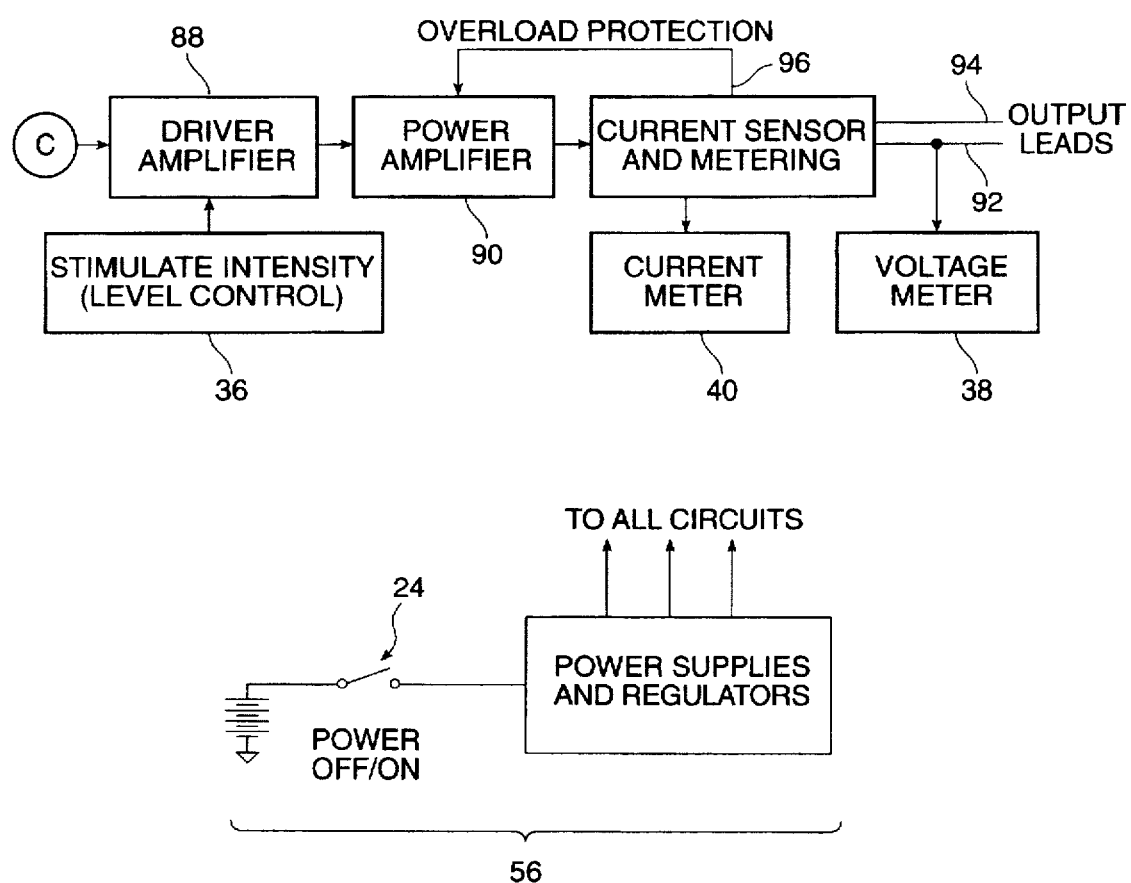
FIG. 6B is a second portion of a schematic block diagram of a presently preferred embodiment of an apparatus according to the invention.

The control unit 10 for the nerve function diagnosis system according to a presently preferred embodiment of the present invention is shown in FIG. 1. The rear of control unit 10 is shown in FIG. 2. Ground pad 12, probe 14 (collectively, "electrodes") and GSR electrodes 16, 18 (preferably utilizing hook and loop type fasteners for closure) are all connected by electrical wires to control unit 10. Battery compartment 20 is located at the rear as shown and preferably includes storage space for the above-described items 12, 14, 16 and 18. The unit 10 is preferably battery powered for convenience, however, an AC power supply could be used instead. FIG. 3 shows the control panel 22 for control unit 10. FIG. 4 shows GSR electrodes 16 and 18 as they would be attached to a patient's fingers according to a presently preferred embodiment of the present invention. FIG. 5 shows the patient as he/she would be connected to the apparatus for testing and measuring current perception threshold and motor nerve junction performance. FIGS. 6A and 6B show first and second portions, respectively, of a schematic block diagram of the control unit 10.

Turning now to FIG. 2, the operation of the apparatus will be discussed with reference to the probes. The apparatus is intended to be connected to the patient with four leads. These are the ground pad 12, probe 14 and the two GSR electrodes 16, 18. Ground pad 12 is preferably a flat square absorbent pad, such as a sponge, having a preferred minimum dimension of 2 inches by 2 inches (4 sq. in), and, more preferably, a size of 4 inches by 4 inches (16 sq. in.) or larger. A round pad or other shape would work as well. The key is that the pad be able to be wetted with water, saline solution, or an equivalent to form a relatively good and stable electrical connection to the body. In normal use, the ground pad 12 is located over the spine (axial) and the patient reclines against it. Probe 14 is preferably a pointed probe having a small contact area. The contact area is preferably wetted with water, saline solution, or an equivalent to form a relatively good electrical connection to the body when pressed against a point on the skin of the body. A gold plated probe with about a one cm long moistened (water, saline or equivalent) fibrous tip is presently preferred for use as probe 14. Other electrode designs would also work in conjunction with the basic invention. Use of the ground pad 12 permits the use of the probe 14 at opposite points of the body (e.g., right thumb tip, left thumb tip) to determine the relative nerve function from those points back to the ground pad 12. Ground pad 12 is preferably not adhered with tape or other adhesives to the body, nor is it sharp or in any way uncomfortable to the patient. With the patient lying on the pad probe 12, a constant pressure is applied and while the pad remains moist, a relatively stable electrical connection to the body is assured.

Turning now to FIG. 3, the operation of the apparatus will be discussed with reference to control panel 22. A main power switch 24 operates in a conventional manner to provide and interrupt power to the unit. The current perception threshold test controls are clustered together at 26. These include a bank of three switches 28, 30 and 32 and a knob 34. Depressing any of switches 28, 30 and 32 will activate the depressed switch while deactivating the other two switches of the three. For testing type A-Beta nerves, switch 28 controls application of a 2000 Hz sine wave electrical signal with a peak current intensity of about 11 mA across the circuit formed by ground pad 12, probe 14, and the patient. Knob 36, labelled "stimulus intensity" controls and limits the peak current intensity, preferably from a level of 0 mA to full scale at 11 mA. The voltage between electrodes 12 and 14 is displayed at voltage meter 38 and the current flowing in probes 12 and 14 is displayed on current meter 40. Knob 34 controls application of an amplitude modulation signal modulating the 2000 Hz signal applied upon depression of switch 28. Preferably the range of amplitude modulation is from about 5 Hz to about 600 or 700 Hz. This modulation has been found to increase the perceptibility of the 2000 Hz signal and in use is dialed to a position which is most perceptible to a particular patient.

For testing type A-Delta nerves, switch 30 controls application of 250 Hz sine wave electrical signal with a peak current intensity of about 9 mA across the circuit formed by ground pad 12, probe 14 and the patient. In this mode, knob 36 controls the peak current intensity, preferably from a level of 0 mA to full scale at 9 mA.

For testing type C nerves, switch 32 controls application of 5 Hz sine wave electrical signal with a peak current intensity of about 9 mA across the circuit formed by ground pad 12, probe 14 and the patient. In this mode, knob 36 controls the peak current intensity, preferably from a level of 0 mA to full scale at 9 mA. Knob 34 does not operate with switches 30 or 32.

A Somato-Kinetic Motor test function is also provided with the apparatus according to a presently preferred embodiment of the present invention. The controls for this function are located at 42 and include switches 44, 46 and 48. Depressing switch 44 causes application of a 250 Hz square wave electrical signal with a peak current intensity of about 9 mA across the circuit formed by ground pad 12, probe 14 and the patient. A sine wave or other waveform signal could also be used. In this mode, knob 36 controls the peak current intensity, preferably from a level of 0 mA to full scale at 9 mA. In conjunction with switch 44, switch 46 operates to interrupt current flow as in a make/break switch. This switch may also be remoted to the handheld probe 14 for ease of use and may be a momentary contact switch so that current flows when it is depressed. This makes it easy to test neuro-muscular responses at specific sites—the muscles twitch upon application of current. Switch 48 provides added functionality by reversing the polarity of probes 12 and 14. By providing this added functionality into a single unit with the CPT testing function the clinician now has at hand a unit which can literally test all of the nerve components of the nerve root.

The GSR function operates as follows. Because it has been found that reliable results are not always forthcoming where an audible patient response is required in order to determine at what current level the signal is detectable by the patient, a galvanic skin resistance system, similar to that used in common lie detectors, is used. An analog GSR meter 50 is provided. The needle is centered while the patient is at rest and unstimulated with knob 52. Sensitivity is controlled over three (or more, if desired) ranges by sensitivity control 54. This allows verification of a patient's verbal report of acquisition of a threshold stimulus by means of monitoring a subconscious reflex biological change in the skin's resistance to electrical current flow. For example, a rested (for 15 minutes) supine patient reports a threshold is first felt at meter reading X using a conventional electrode system. The patient may then be connected to the GSR electrodes and monitored for GSR stability. A series of increasing intensity stimuli is then given to the patient to determine if the same reported threshold level of stimulation causes a biological reaction in the GSR. When a patient is quietly resting, a threshold stimulus will disturb the resting state and be detectable as a change in GSR activity. It is also possible to do away altogether with audible patient input in the testing process using this mechanism.

Turning now to FIGS. 6A–6B, a schematic block diagram of the apparatus of the present invention is set forth. Conventional power supplies and voltage regulators powered by a battery pack switched by on-off switch 24 are detailed at 56. The GSR circuit is detailed at 58. The GSR leads 60, 62 from GSR electrodes 16, 18 are connected to a conventional Wheatstone Bridge circuit 64 to which is applied a differential DC current source 66 and a value from GSR center control 52. The output of the Wheatstone Bridge circuit 64 is directed to a Differential DC Voltmeter circuit 70 which is further controlled by GSR sensitivity switch 54 and drives GSR Meter 50.

The balance of the circuitry is described as follows. A Keyboard Decoder and Function Selector 72 accepts as inputs the switches 28, 30, 32, 44, 46 and 48, as shown. A 2000 Hz, a 250 Hz and a 5 Hz oscillators 74, 76 and 78 are provided. An adjustable 5 Hz–600 (or 700) Hz oscillator 80 is also provided together with an amplitude modulation circuit 82 so that adjustable oscillator 80 can be used to modulate 2000 Hz oscillator 74. Anode/cathode reversal switch 48 controls a polarity inverter circuit 84 which simply reverses the connections between the two electrodes. A 250 Hz pulse generator (squarewave output) 86 is activated by switch 44 to provide the somato kinetic motor test signal. A sine wave output may also be used but squarewaves are presently preferred. An intermediate signal output is provided at "C" on FIG. 6A. At "C" on FIG. 6B, the intermediate signal is amplified by driver amplifier 88 under control of stimulus intensity control 36. The output is then provided to power amplifier 90. The output of power amplifier 90 is directed to current sensor and metering circuits which drive voltage meter 38, current meter 40 and output leads 92, 94 which connect to electrodes 12, 14. Foldback overload protection as shown at 96 preferably protects power amplifier 90 and prevents excess voltage/current conditions on output leads 92, 94.

While illustrative embodiments and applications of this invention have been shown and described, it would be apparent to those skilled in the art that many more modifications than have been mentioned above are possible without departing from the inventive concepts set forth herein. The invention, therefore, is not to be limited except in the spirit of the appended claims.

What is claimed is:

1. An apparatus for testing and measuring current perception threshold in selected nerve fiber groups of a patient, said apparatus comprising:

a waveform generator for generating a current-limited electrical signal;

means for varying an electrical current magnitude of said electrical signal among a plurality of values;

a single first electrode comprising an absorbent pad of at least about 4 square inches in surface area and capable of being moistened to enhance electrical contact with the skin of the patient;

a single second electrode adapted to be placed at a distance from said first electrode;

the apparatus adapted to cause said electrical signal to pass through said first electrode, the selected nerve fiber groups of the patient, and said second electrode;

threshold detection means for detecting a threshold current magnitude at which the selected nerve fiber groups of the patient first perceive said electrical signal; and means for displaying an indication of said electrical current magnitude corresponding to the current perception threshold.

2. An apparatus according to claim 1 wherein said second electrode is a handheld electrode including a fibrous tip which may be moistened to enhance electrical contact with the skin of the patient.

3. An apparatus according to claim 1 wherein said electrical signal is a sine wave.

4. An apparatus according to claim 1 wherein said electrical signal is a sine wave amplitude modulated by another sine wave.

5. An apparatus for testing and measuring current perception threshold in selected type A-Beta nerve fiber groups of a patient, said apparatus comprising:

a waveform generator for generating a repeating current-limited electrical signal of approximately 2000 Hz in frequency;

means for amplitude modulating said electrical signal with a modulating signal having a frequency adjustable in the range of about 5 Hz to about 700 Hz;

means for varying an electrical current magnitude of said electrical signal among a plurality of values;

a single first electrode;

a single second electrode;

the apparatus adapted to cause said electrical signal to pass through said first electrode, the selected type A-Beta nerve fiber groups of the patient, and said second electrode;

threshold detection means for detecting a threshold current magnitude at which the selected type A-Beta nerve fiber groups of the patient first perceive said electrical signal; and means for displaying an indication of said electrical current magnitude corresponding to the current perception threshold.

6. An apparatus according to claim 5 wherein said modulating signal is a sine wave.

7. An apparatus according to claim 5 wherein said first electrode is an absorbent pad of at least about 4 square inches in surface area.

8. An apparatus according to claim 6 wherein said first electrode is an absorbent pad of at least about 4 square inches in surface area.

9. An apparatus according to claim 7 wherein said second electrode is a handheld electrode including a fibrous tip which may be moistened to enhance electrical contact with the skin of the patient.

10. An apparatus according to claim 8 wherein said second electrode is a handheld electrode including a fibrous tip which may be moistened to enhance electrical contact with the skin of the patient.

11. An apparatus for testing and measuring current perception threshold in selected nerve fiber groups of a patient, said apparatus comprising:

a waveform generator for generating a repeating current-limited electrical signal having a selected frequency in the range of about 5 Hz to about 2000 Hz;

means for varying an electrical current magnitude of said electrical signal among a plurality of values;

a single first and a single second current perception threshold electrode;

a first and a second separate galvanic skin response electrode;

the apparatus adapted to cause said electrical signal to pass through said first current perception threshold electrode, the selected nerve fiber groups of the patient, and said second current perception threshold electrode;

threshold detection means for detecting a threshold current magnitude at which the selected nerve fiber groups of the patient first perceive said electric signal, said threshold detection means responsive to a change in patient skin resistance measured between said first and second galvanic skin response electrodes; and means for displaying an indication of said electrical current magnitude corresponding to the current perception threshold.

12. An apparatus for testing and measuring current perception threshold in selected nerve fiber groups of a patient, said apparatus comprising:

a waveform generator for generating a repeating current-limited electrical signal;

means for varying an electrical current magnitude of said electrical signal among a plurality of values;

a single first current perception threshold electrode comprising an absorbent pad of at least 4 square inches in surface area;

a single second current perception threshold electrode adapted to be placed at a distance from said first current perception threshold electrode;

a first and a second galvanic skin response electrode separate from said first and second current perception threshold electrodes;

the apparatus adapted to cause said electrical signal to pass through said first current perception threshold electrode, the selected nerve fiber groups of the patient, and said second current perception threshold electrode;

threshold detection means for detecting a threshold current magnitude at which the selected nerve fiber groups of the patient first perceive said electric signal, said threshold detection means responsive to a change in patient skin resistance measured between said first and second galvanic skin response electrodes; and means for displaying an indication of said electrical current magnitude corresponding to the current perception threshold.

13. An apparatus according to claim 11 wherein said second electrode is a handheld electrode including a fibrous tip which may be moistened to enhance electrical contact with the skin of the patient.

14. An apparatus according to claim 12 wherein said second electrode is a handheld electrode including a fibrous tip which may be moistened to enhance electrical contact with the skin of the patient.

15. An apparatus according to claim 11 further comprising means for amplitude modulating said electrical signal with a modulating signal having a frequency adjustable in the range of about 5 Hz to about 700 Hz.

16. An apparatus according to claim 12 further comprising means for amplitude modulating said electrical signal with a modulating signal having a frequency adjustable in the range of about 5 Hz to about 700 Hz.

17. A method for measuring a current perception threshold in a selected nerve fiber group of a patient, said method comprising:

(a) applying a single first electrode comprising an absorbent pad of at least about 4 square inches in surface area to the back of the patient along the patient's spine;

(b) moistening said first electrode;

(c) applying a single second electrode to a first selected point on the skin of the patient, said point selected so as to measure the selected nerve fiber group;

(d) generating a repeating current-limited electrical signal with a waveform generator;

(e) causing said electrical signal to pass through said first electrode, the selected nerve fiber group, and said second electrode;

(f) adjusting the current of said electrical signal among a plurality of values and detecting a current magnitude at which the selected nerve fiber group of the patient first perceives said electrical signal;

(g) displaying said current magnitude at which the selected nerve fiber group of the patient first perceives said electrical signal.

18. A method for measuring a current perception threshold in a selected type A-Beta nerve fiber group of a patient, said method comprising:

(a) applying a single first electrode comprising an absorbent pad of at least about 4 square inches in surface area to the back of the patient along the patient's spine;

(b) moistening said first electrode;

(c) applying a single second electrode to a first selected point on the skin of the patient, said point selected so as to measure the selected type A-Beta nerve fiber group;

(d) generating a repeating current-limited electrical signal with a waveform generator having a frequency of approximately 2000 Hz;

(e) amplitude modulating said electrical signal with a modulating signal having a frequency adjustable in the range of about 5 Hz to about 700 Hz;

(f) causing said electrical signal to pass through said first electrode, the selected type A-Beta nerve fiber group, and said second electrode;

(g) adjusting the current of said electrical signal among a plurality of values and detecting a current magnitude at which the selected nerve fiber group of the patient first perceives said electrical signal;

(h) displaying said current magnitude at which the selected nerve fiber group of the patient first perceives said electrical signal.

19. A method for measuring a current perception threshold in a selected nerve fiber group of a patient, said method comprising:

(a) applying a single first electrode to the patient;

(b) applying a single second electrode to a first selected point on the skin of the patient, said point selected so as to measure the selected nerve fiber group;

(c) generating a repeating current-limited electrical signal with a waveform generator having a selected frequency in the range of about 5 Hz to about 2000 Hz;

(d) causing said electrical signal to pass through said first electrode, the selected nerve fiber group, and said second electrode;

(e) applying a separate pair of galvanic skin resistance electrodes to the skin of the patient and monitoring skin resistance values measured by said resistance electrodes;

(f) adjusting the current of said electrical signal among a plurality of values and detecting a current magnitude at which the selected nerve fiber group of the patient first achieves perception of said electrical signal, said perception determined to have occurred at a point in time when said skin resistance values change by more than a predetermined amount; and (g) displaying said current magnitude at which the selected nerve fiber group of the patient first perceives said electrical signal.

20. A method according to claim 17 further comprising the steps of:

(h) applying said single second electrode to a second selected point on the skin of the patient, said second selected point selected so as to be at an opposite point of the patient's body from said first selected point, so as to measure a nerve fiber group opposite said selected nerve fiber group;

(i) generating a repeating current-limited electrical signal with a waveform generator;

(j) causing said electrical signal to pass through said first electrode, the opposite selected nerve fiber group, and said second electrode;

(k) adjusting the current of said electrical signal among a plurality of values and detecting a current magnitude at which the opposite selected nerve fiber group of the patient first perceives said electrical signal; and (l) displaying said current magnitude at which the opposite selected nerve fiber group of the patient first perceives said electrical signal.

21. A method according to claim 18 further comprising the steps of:

(i) applying said single second electrode to a second selected point on the skin of the patient, said second selected point selected so as to be at an opposite point of the body from said first selected point, so as to measure a type A-Beta nerve fiber group opposite said selected type A-Beta nerve fiber group;

(j) generating a repeating current-limited electrical signal with a waveform generator having a frequency of approximately 2000 Hz;

(k) amplitude modulating said electrical signal with a modulating signal having a frequency adjustable in the range of about 5 Hz to about 700 Hz;

(l) causing said electrical signal to pass through said first electrode, the opposite selected type A-Beta nerve fiber group, and said second electrode;

(m) adjusting the current of said electrical signal among a plurality of values and detecting a current magnitude at which the opposite selected nerve fiber group of the patient first perceives said electrical signal; and (n) displaying said current magnitude at which the opposite selected nerve fiber group of the patient first perceives said electrical signal.

22. A method according to claim 19 wherein said first electrode is applied to the back of the patient along the patient's spine, said method further comprising the steps of:

(h) applying said single second electrode to a second selected point on the skin of the patient, said second selected point selected so as to be at an opposite point of the body from said first selected point, said second point selected so as to measure current perception threshold in a nerve fiber group opposite said selected nerve fiber group;

(i) generating a repeating current-limited electrical signal with a waveform generator having a selected frequency in the range of about 5 Hz to about 2000 Hz;

(j) causing said electrical signal to pass through said first electrode, the opposite selected nerve fiber group, and said second electrode;

(k) applying a pair of galvanic skin resistance electrodes to the skin of the patient and monitoring skin resistance values measured by said resistance electrodes;

(l) adjusting the current of said electrical signal among a plurality of values and detecting a current magnitude at which the opposite selected nerve fiber group of the patient first achieves perception of said electrical signal, said perception determined to have occurred at a point in time when said skin resistance values change by more than a predetermined amount; and (m) displaying said current magnitude at which the opposite selected nerve fiber group of the patient first perceives said electrical signal.

* * * * *